United States Patent [19]

Schumacher et al.

[11] Patent Number: 5,496,285
[45] Date of Patent: Mar. 5, 1996

[54] DISPOSABLE SYRINGE

[75] Inventors: Herbert Schumacher, Gorxheimertal; Norbert Messner, Neustadt; Ernst Osen, Birkenau; Dirk Ecknig, Mannheim, all of Germany

[73] Assignee: Firma Carl Freudenberg, Weinheim, Germany

[21] Appl. No.: 341,816

[22] Filed: Nov. 18, 1994

[30] Foreign Application Priority Data

Nov. 19, 1993 [DE] Germany .................. 43 39 528.7

[51] Int. Cl.⁶ .................................................. A61M 5/315
[52] U.S. Cl. ........................................... 604/218; 604/228
[58] Field of Search ........................... 604/218, 222, 604/221, 228, 187

[56] References Cited

U.S. PATENT DOCUMENTS

| | | | |
|---|---|---|---|
| 4,057,052 | 11/1977 | Kaufman et al. | 604/218 X |
| 4,266,557 | 5/1981 | Merry | 604/222 X |
| 4,303,070 | 12/1981 | Ichikawa et al. | 604/222 |
| 4,354,507 | 10/1982 | Raitto | 604/218 X |
| 4,704,105 | 11/1987 | Adorjan et al. | 604/222 |
| 5,061,252 | 10/1991 | Dragosits | 604/218 |

Primary Examiner—John D. Yasko
Attorney, Agent, or Firm—Kenyon & Kenyon

[57] ABSTRACT

A disposable syringe for administering liquid medicinal agents to live animal or human subjects is disclosed. The syringe comprises a hollow cylinder, filled with a medicinal agent, with which an injection needle is attached. The cylinder surrounds a piston that can be moved by means of a piston rod towards the injection needle. The piston is produced from a thermoplastically processable rubber mixture and is delimited in the direction of the medicinal agent by a peripheral sealing lip that contacts the hollow cylinder and that can be deflected in the radial direction.

14 Claims, 6 Drawing Sheets

DISPOSABLE SYRINGE

BACKGROUND OF THE INVENTION

The invention generally relates to a disposable syringe for administering liquid medicinal agents to live animal or human subjects. Generally speaking, the syringe comprises a hollow cylinder filled with a medicinal agent that terminates with an injection needle. The cylinder surrounds a piston that can be moved by means of a piston rod toward the injection needle.

Disposable syringes of this kind are generally known. Typically, the piston and the piston rod are configured of a single material and are integrally and continuously linked with one another. The piston rod and piston are made, for example, of polyethylene or nylon; the hollow cylinder preferably is made of polyethylene. However, the arrangement often provides an unsatisfactory sealing effect between the piston and the hollow cylinder. Even when very tight manufacturing tolerances are maintained, the pressure of the piston against the inner wall of the hollow cylinder varies among peripherally adjacent subregions of the piston. This increases the risk of leakage due to relaxation phenomena within the piston. Moreover, the cylindrical piston has on the side facing the medicinal agents a flat end wall extending in the radial direction, which prevents the full discharge of the contents of the hollow cylinder.

There remains a need to further develop a disposable syringe of the aforesaid type so that the above-identified shortcomings are avoided. There further remains a need for such a syringe having improved operating characteristics. In particular, there remains a need to improve the sealing between the piston and the hollow cylinder so as to prevent leaks in this region and so that medicinal agent can be discharged almost completely from the hollow cylinder.

SUMMARY OF THE INVENTION

In the present invention, the piston is produced from a thermoplastically processable rubber mixture. It is delimited in the direction of the medicinal agent by a peripheral sealing lip that contacts the hollow cylinder and which can be deflected in the radial direction. The piston is configured as a sealing element and is made of an elastomeric rubber material, so that the sealing lip, which is resilient in the radial direction, is in sealing engagement with the inner surface of the hollow cylinder. The sealing lip contacts the hollow cylinder on the inside along a circumferential line with a consistent radial preload. Manufacturing-related tolerances of the hollow cylinder and/or the piston can thereby easily be compensated for, thus resulting in reliable sealing.

Still greater security against the unwanted loss of medicinal agent via leakage can be obtained by using a plurality of sealing lips arranged in functional succession in the direction of the piston rod movement. On the other hand, the use of only one such peripheral sealing lip has the advantage of minimizing any friction between the piston and the hollow cylinder so as to provide a smooth, low-force actuation of the piston rod. With such an arrangement, the medicinal agent being administered can be metered easily and precisely.

According to one embodiment, the piston can be fastened by means of internal threads to external threads of the piston rod, the internal threads preferably being shorter in the movement direction of the piston than the external threads. The piston rod is preferably configured with a dished pressure plate on the side facing away from the medicinal agent.

The shaft of the piston rod preferably has a cruciform cross section. The cruciform cross section reliably eliminates the risk of bending the shaft during actuation, especially when the piston rod is used in hollow cylinders with small diameters and/or with viscous medicinal agents.

Arranged adjacent to the shaft on the side facing the medicinal agent is a dished support washer that is configured integrally and continuously with the piston rod and delimits, with the inner surface of the hollow cylinder, an annular gap. Low-friction relative mobility of the piston rod within the hollow cylinder is assured because the support washer does not lie in contact with the inside diameter of the hollow cylinder along its entire outer periphery.

By fastening the piston to the piston rod by means of a threaded joint, there is obtained enhanced relative immobility of the two parts with respect to one another in the axial direction, which is advantageous in helping to provide an exact metering of the substance being administered. A prerequisite for ensuring this kind of mutually immobile fastening of the two parts to one another is that the internal threads and external threads be fastened to one another without axial play, i.e., with a degree of axial preload. An axial preload of this kind can be effected, for example, by providing that the internal threads of the piston be shorter in the latter's movement direction than the external threads of the piston rod. The substantially cup-shaped piston is threaded onto the external threads of the piston rod until the bottom surface of the piston is in contact with the end surface of the piston rod (which constitutes the end of the external threads) with an elastic preload. The elastomeric material of the internal threads is thereby braced against the turns of the external threads of the piston rod, thus eliminating the thread play.

According to another embodiment, the internal threads can be longer in the movement direction of the piston than the external threads. This is advantageous in that when the cup-shaped piston is threaded onto the external threads of the piston rod, the annular surface of the piston first comes into contact with the support washer of the piston rod. When the piston is then threaded further onto the external threads of the piston rod, until the bottom contacts the end surface, the support washer, designed as a buttress, produces bulging of the elastomeric material of the piston on the side opposite the medicinal agent, and a radial deflection movement, so that the bulged material contacts and seals against the inner periphery of the hollow cylinder. This embodiment not only eliminates thread play, but also further improves protection against fluid losses.

According to another embodiment, the piston can be fastened by means of external threads to internal threads of the piston rod, the internal threads being shorter along the axial direction of piston movement than the external threads of the piston. One advantage of this arrangement is that radial deflection movements of the elastomeric material of the piston do not occur upon fastening to the piston rod in the direction of the hollow cylinder, thus reliably eliminating high actuation forces and immobilization of the piston in the hollow cylinder. The piston is threaded into the piston rod until the turns of the external threads and the turns of the internal threads are braced against one another.

The rubber mixture can consist predominantly of a block polymer, and can contain a quantity of a polyolefin. Such a composition of rubber mixture advantageously provides good resilience, while presenting minimal relaxation phenomena in the course of use. Furthermore, a rubber mixture of this kind is easily and economically manufactured. It is also advantageous that a block polymer with a polyolefin quantity is resistant to the most common medicinal agents. Polypropylene can be used as the polyolefin, the quantity preferably being 1 to 30 wt %. The resilience of the piston can be adapted to the particular conditions of the application as a function of the quantity of polypropylene in the rubber mixture. For example, if a comparatively viscous medicinal agent is to be administered, it has proven to be advantageous that the polypropylene quantity be 20 to 30 wt %, which provides the piston with the required rigidity.

To improve the sliding characteristics of the piston in the hollow cylinder, the rubber mixture can contain a quantity of 0.1 to 2 wt % of a silicone rubber. The improved sliding characteristics eliminate stick-slip effects. Operation of the disposable syringe is simplified, and the medicinal agent can be administered in accurately predetermined doses.

The rubber mixture can be composed predominantly of an at least partially crosslinked rubber and a thermoplastic material, the rubber mixture being, for example, composed of styrene-ethylene-butylene-styrene (SEBS).

The sealing lip can have at least one sealing edge that is preferably delimited on the outside by two conical surfaces that intersect one another. In an embodiment of this kind, the sealing edge extends along the piston substantially linearly and on the outer circumference, and reliably seals off the inner wall of the hollow cylinder. According to a further embodiment, the sealing edge is delimited on the outside by a surface with a semicircular cross section. An embodiment of this kind is particularly advantageous when the radial pressure of the sealing lip against the hollow cylinder and/or the pressure inside the hollow cylinder is relatively elevated by administration of the medicinal agent. As a result, the sealing lip is better protected against abrasive wear and therefore seals optimally even under such conditions.

The piston can be provided with a recess radially inside the sealing lip. The recess preferably consists of a peripheral groove penetrating into the end surface of the piston. During movement of the piston rod in the direction of the injection needle and injection of the medicinal agent, excess pressure relative to the atmosphere builds up inside the annular peripheral groove, additionally reinforcing the pressure, conditioned by both design and material, of the sealing lip against the inner wall of the hollow cylinder. The pressure of the sealing lip against the hollow cylinder automatically adapts as a function of the viscosity of the medicinal agent and the pressure that thereby builds up inside the hollow cylinder during administration of the medicinal agent.

The piston can have, radially inside the groove, an end surface that has a shape conforming to the end wall of the hollow cylinder. The result of this embodiment is that the dead space inside the hollow cylinder when the piston rod is completely inserted is kept to a minimum. When the disposable syringe is actuated, the end surface of the elastomeric piston is moved almost to the outlet opening of the hollow cylinder, and almost completely displaces the medicinal agent present in the hollow cylinder.

The end surface preferably delimits a projection that extends beyond the sealing lip in the direction of the end wall. As a result, liquid components of the medicinal agent that are located in the narrowed outlet region of the hollow cylinder are almost completely administered.

The excess length of the projection formed by the extended end can, according to one embodiment, be dimensioned so that the radial displacement of the sealing lip that results when the piston is pressed against the end wall substantially fills the groove. The liquid components of the medicinal agent that are located inside the groove during movement of the piston rod toward the injection needle are forced out of the groove toward the injection needle, as the piston comes to a stop against the end wall of the hollow cylinder, by the elastic deformation of the piston. This ensures that despite the deformation of the piston, no liquid components of the medicinal agent are forced past the sealing lip toward the atmosphere.

The end surface can be interrupted by at least one recess, running radially, that extends from the outer circumference to the center. This assures that the medicinal agent is not enclosed in cavities when the end of the piston comes to a stop against the end wall of the hollow cylinder, but rather that a liquid-carrying connection toward the injection needle always exists.

BRIEF DESCRIPTION OF THE DRAWINGS

An embodiment of a disposable syringe constructed according to the principles of the invention will be explained below in greater detail with reference to the drawings.

DETAILED DESCRIPTION

Figure 1:
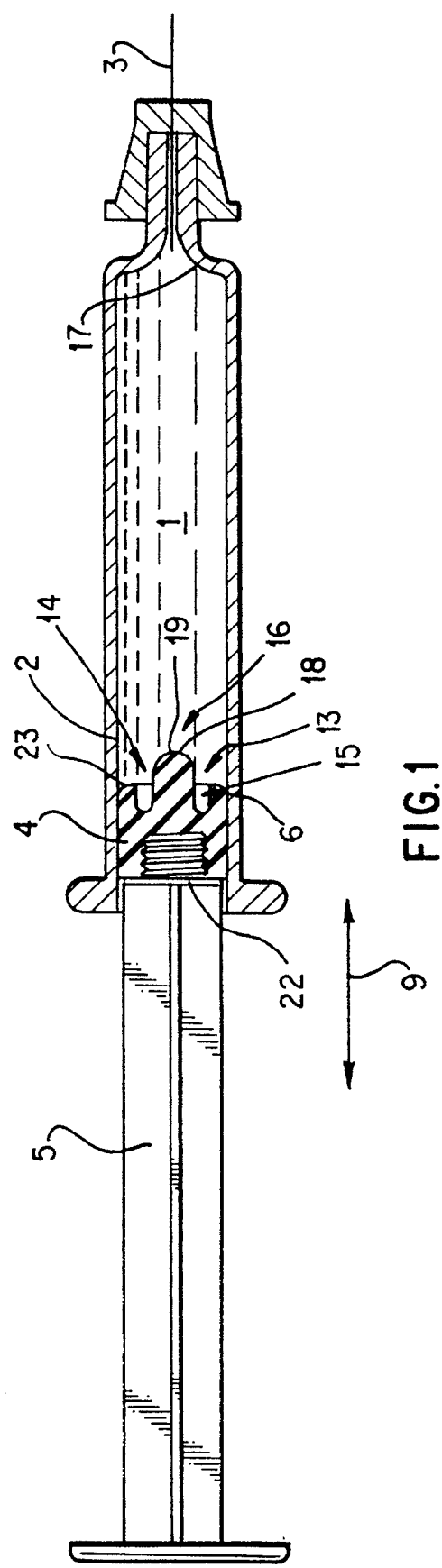
FIG. 1 is a longitudinal view in cross section of the disposable syringe of the invention, filled with a medicinal agent.

FIG. 1 shows a first embodiment of a disposable syringe that is filled with a liquid medicinal agent 1. The disposable syringe comprises a hollow cylinder 2, one axial end of which is closed off in a liquid-tight manner by a piston 4 placed on a piston rod 5, and the other axial end of which is provided with an injection needle 3. Piston 4 consists of a resilient, thermoplastically processable rubber material, preferably TPE, and seals the medicinal agent inside the hollow cylinder with respect to the environment. Piston 4 is cup-shaped, and has inside a recess internal threads 7 with which it is mounted onto external threads 8 of piston rod 5. Piston 4 is fastened onto the piston rod under an axial preload, which compensates for thread play. In the embodiment depicted here, the annular rim of piston 4 is in sealing contact with support washer 22 of piston rod 5 under elastic preload, the bulging of the elastomeric material causing a radial expansion and additional sealing against the inner wall of hollow cylinder 2.

Figure 2:
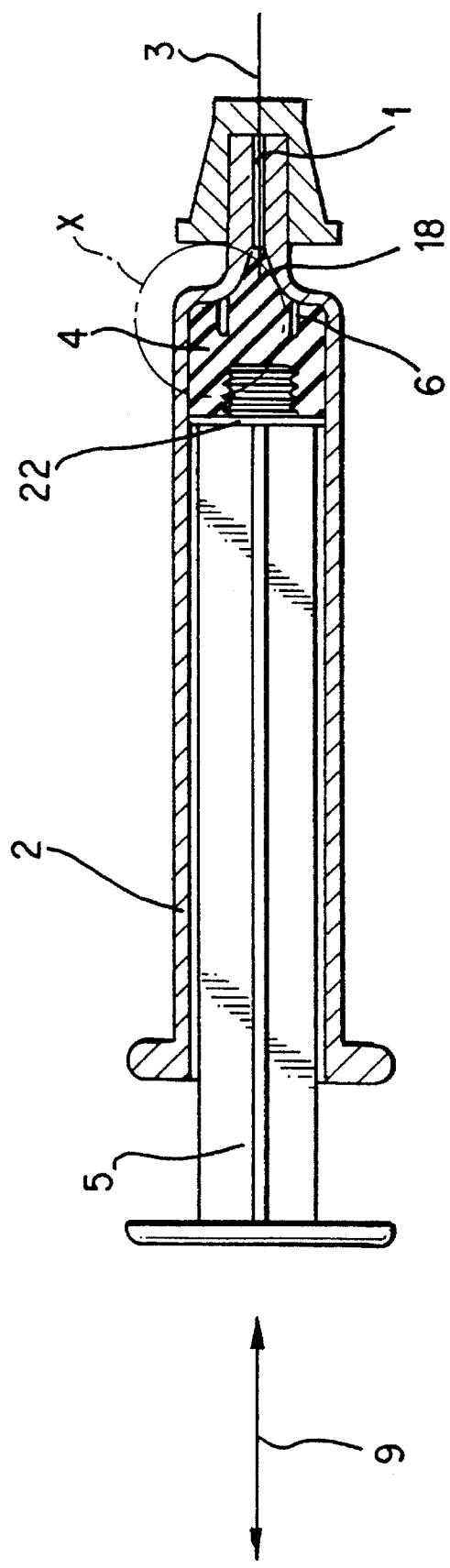
FIG. 2 is a view similar to that of FIG. 1, but with the syringe discharged.

FIG. 2 shows the disposable syringe of the invention in the discharged state. End surface 14 (illustrated in FIG. 3) of piston 4 facing the medicinal agent 1 lies in contact with the inside end wall 17 of the hollow cylinder 2. A projection 18 located at the proximal end of the piston at least partially fills the outlet opening of the hollow cylinder 2.

Figure 3:
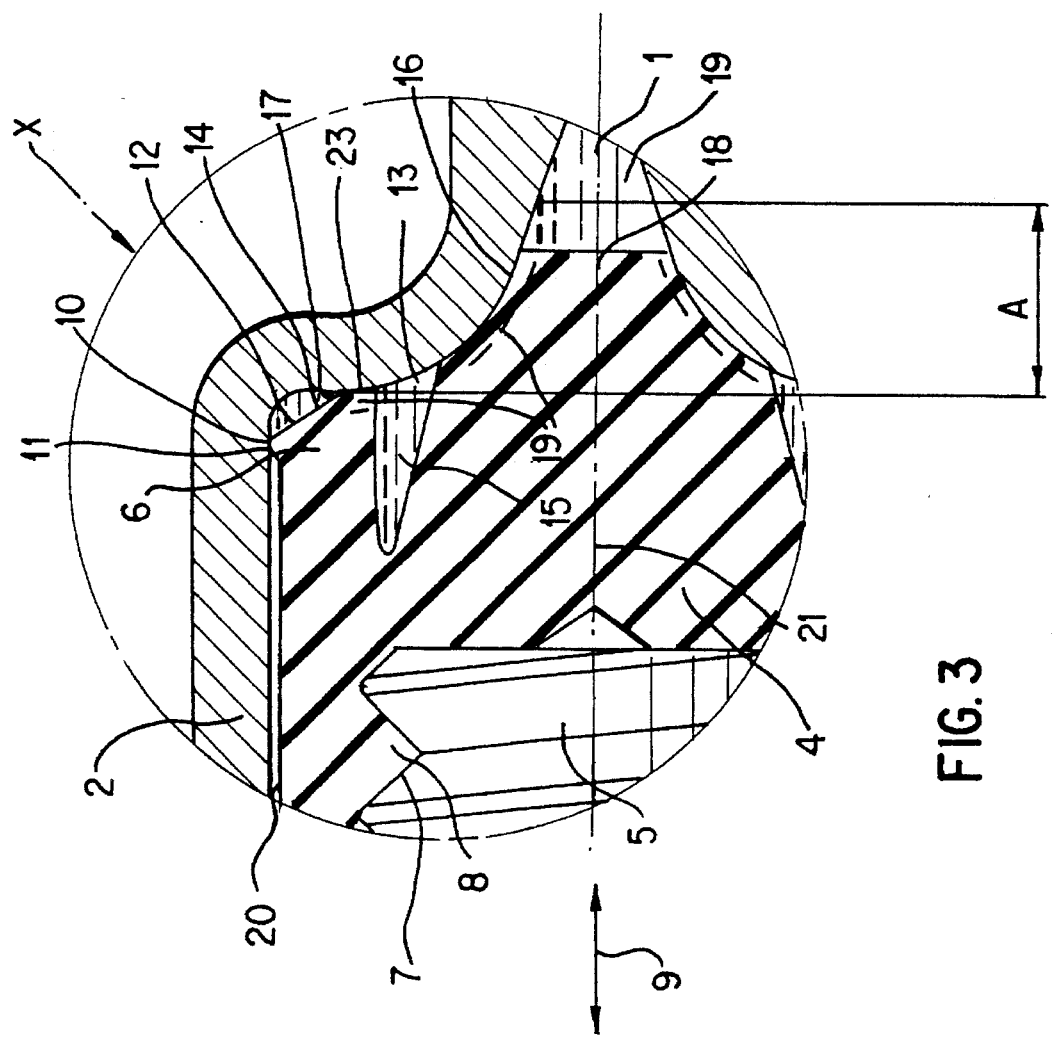
FIG. 3 is a fragmentary sectional view of region X in FIG. 2, showing a section of the disposable syringe just prior to the complete discharge of the medicinal agent.

In FIG. 3 the disposable syringe is depicted in the region of its outlet opening, just prior to the complete discharge of the medicinal agent 1. Piston 4 is in sealing contact with the inner peripheral wall of the hollow cylinder 2, with its sealing lip 6 under a radial preload. In this embodiment sealing lip 6 has a sealing edge 10. Piston 4 also contacts the inner wall of hollow cylinder 2 with a sealing lug 23 radially outside a groove 15, and with end surface 16 radially inside groove 15. In this operating state, projection 18 is centered in the illustrated position by the outlet opening at the proximal end of the hollow cylinder 2. Recesses 19 are provided for delivery of medicinal agent 1 toward injection needle 3, as they channel medicinal agent 1 toward injection needle 3. The recesses extend inside projection 18 in the direction of flow.

Figure 4:
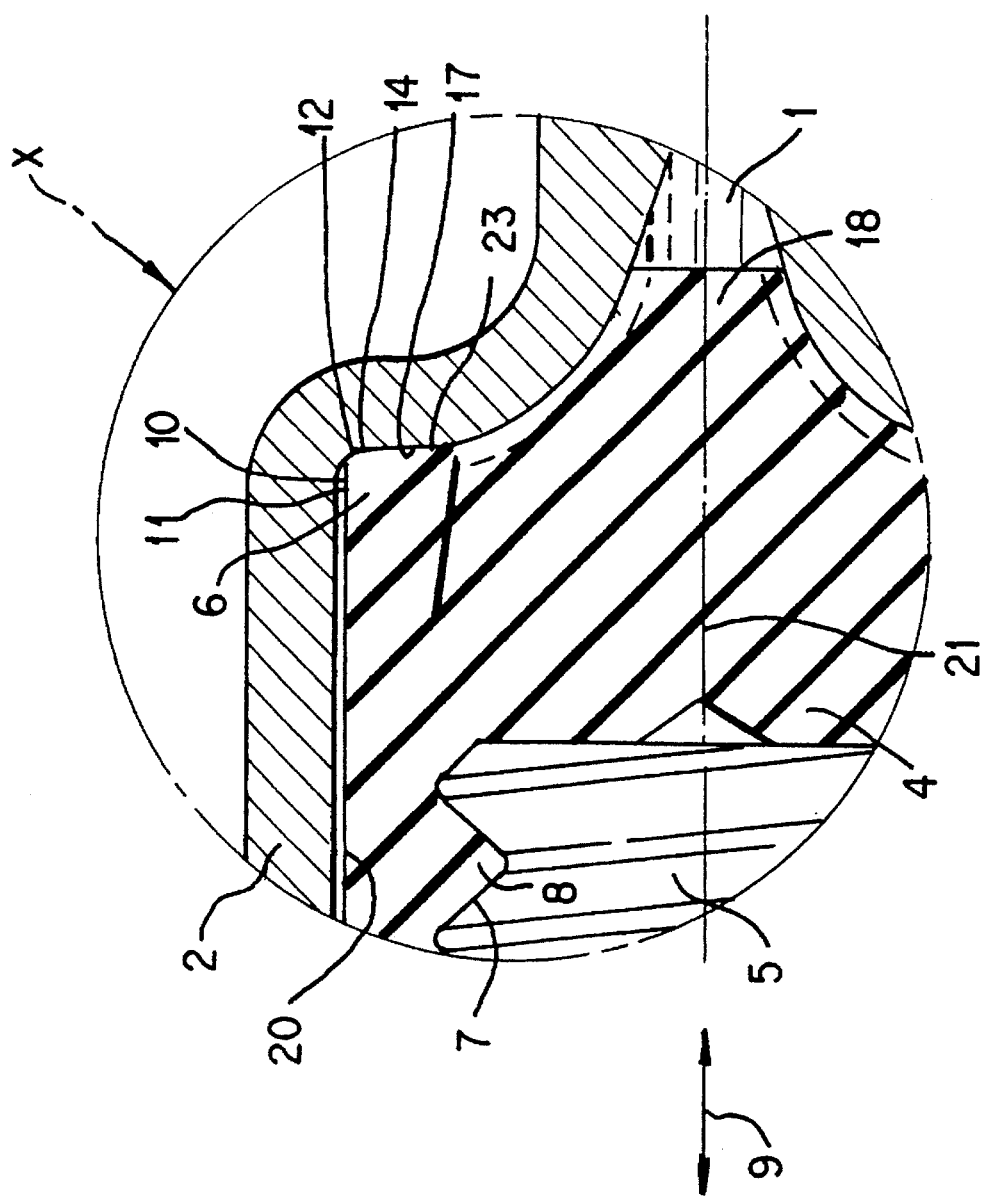
FIG. 4 is a fragmentary view similar to FIG. 3, in which the piston rod has been displaced relatively farther toward the injection needle, and the medicinal agent has been discharged as completely as possible.

FIG. 4 depicts with a level of detail similar to that of FIG. 3 the configuration of the piston 4 when piston rod 5 is moved farther toward the outlet opening of hollow cylinder 2. Proceeding from the depiction of FIG. 3, the subregion of the piston radially outside groove 15 has been displaced radially inwardly as a result of its contact with the inner wall of the hollow cylinder 2. As before, sealing edge 10 of sealing lip 6 is in sealing contact with the hollow cylinder 2. Sealing lug 23 provides guidance of sealing lip 6; because of the radial displacement, groove 15 is substantially closed and the liquid components of medicinal agent 1 located therein are forced through recesses 19 of projection 18 toward the injection needle 3. In this state, When all liquid components of medicinal agent 1 have been forced out of groove 15, piston 4 completely closes off the outlet opening of hollow cylinder 2. Excess piston length A (shown in the figure) must be dimensioned, in conjunction with the geometric configuration of projection 19, in such a way that end surface 14 of piston 4 does not completely close off the outlet opening of hollow cylinder 2 until no further medicinal agent 1 is located radially outside of and in groove 15.

Figure 5:
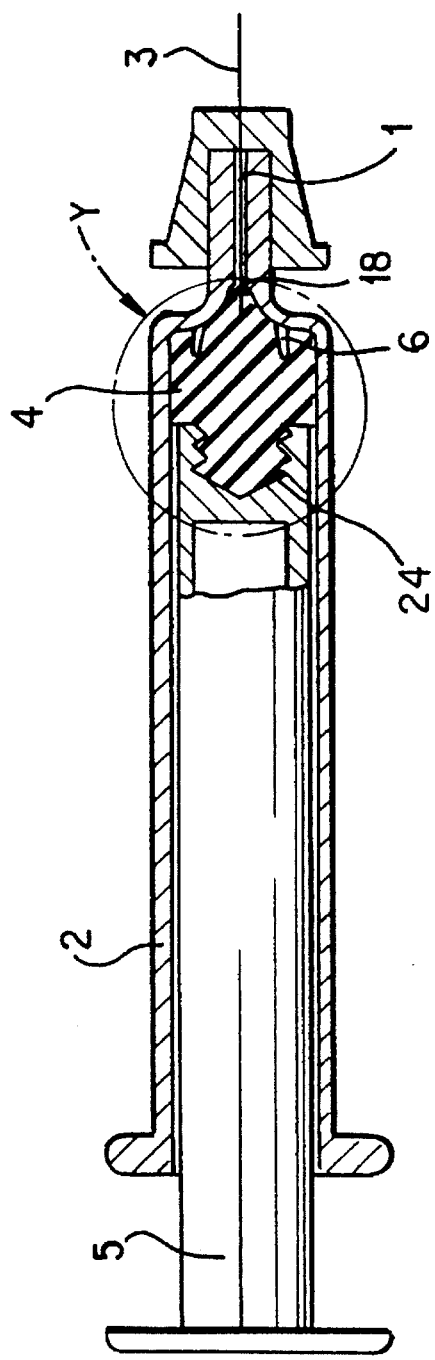
FIGS. 5 and 6 show a further embodiment in which the piston is fastened by external threads in internal threads of the piston rod.

FIG. 5 shows a further embodiment of the disposable syringe according to the invention, in which medicinal agent 1 has been largely discharged. In contrast to the embodiment depicted in FIG. 1, piston 4 has on the side facing away from medicinal agent 1 integrally formed external threads 24. The external threads 24 are joined to internal threads 25 of piston rod 5. End surface 14 of the piston, facing medicinal agent 1, is identical to the corresponding portion of the embodiment of FIG. 3.

Figure 6:
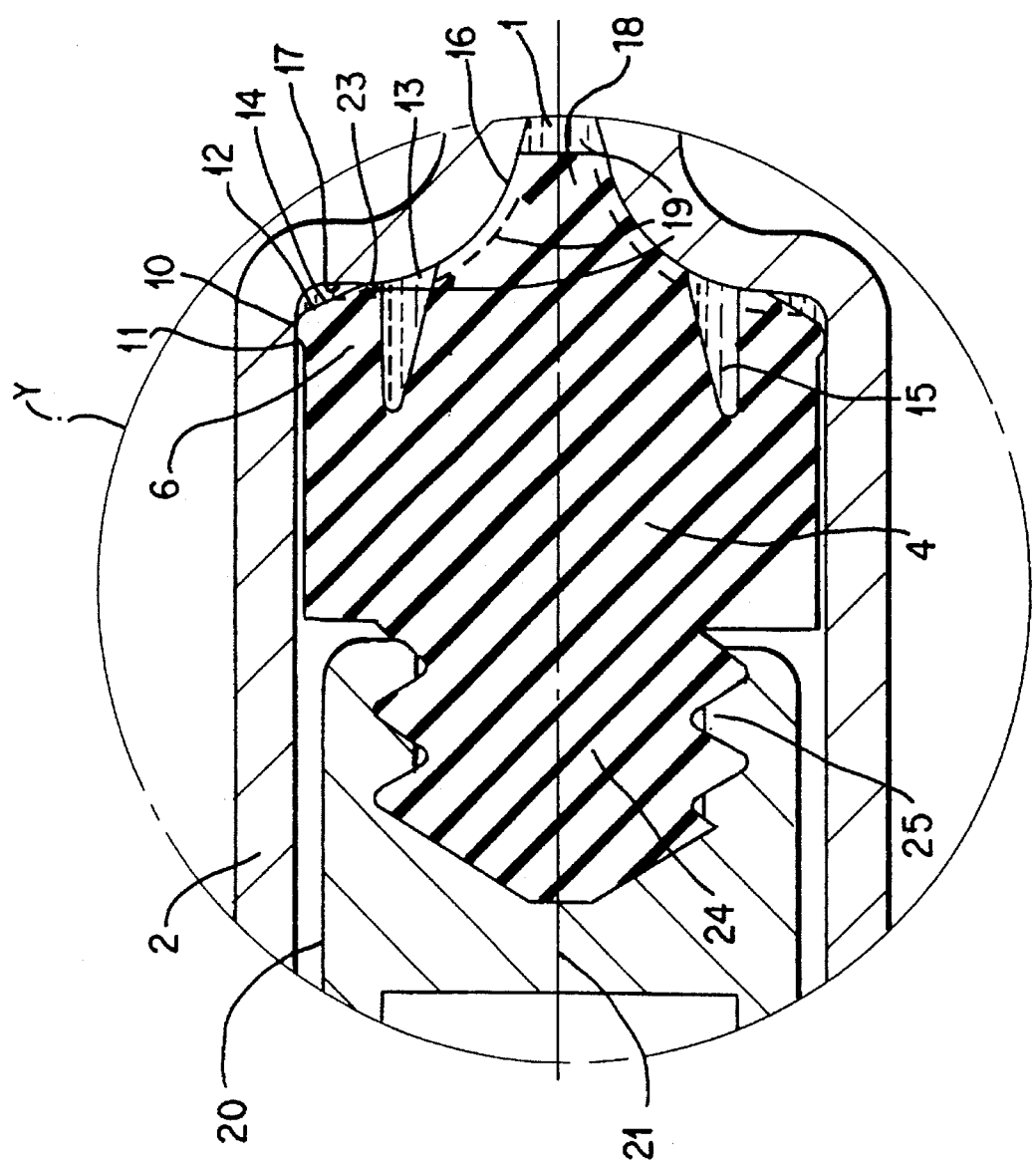

FIG. 6 depicts a section of the disposable syringe of FIG. 5 at enlarged scale. This Figure clearly shows that the outer circumferential surface of piston 4 does not bulge subsequent to assembly, and therefore does not expand radially. The advantage here is that on the outer circumference, piston 4 contacts the inner wall of the hollow cylinder only with sealing edge 10 of sealing lip 6, thus reducing to a minimum the actuation forces necessary to administer an injection.

What is claimed is:

1. A disposable syringe for administering liquid medicinal agents; comprising:

a hollow cylinder having proximal and distal ends, said hollow cylinder being configured to receive a liquid;

an injection needle located at the proximal end of the hollow cylinder;

a piston made from a thermoplastically processable rubber mixture and being delimited in the proximal direction by a radially deflectable peripheral sealing lip, said piston being provided with a recess radially inside the sealing lip; and a piston rod, said piston being located at one end of the piston rod, said piston rod and said piston being configured to be slidable within the hollow cylinder so that the piston can be displaced by the piston rod within the hollow cylinder towards the injection needle at the proximal end of the cylinder;

wherein the peripheral sealing lip on the piston contacts the hollow cylinder and is configured to be radially deformed so as to reduce the recess when driven by the piston rod towards the proximal end of the hollow cylinder.

2. A disposable syringe according to claim 1, wherein the piston is fastened by means of internal threads to external threads on the piston rod, said internal threads being axially shorter than the external threads of the piston rod.

3. A disposable syringe according to claim 1, wherein the piston is fastened by means of external threads to internal threads on the piston rod, said internal threads being axially shorter than the external threads of the piston.

4. A disposable syringe according to claim 1, wherein the rubber mixture consists predominantly of a block polymer.

5. A disposable syringe according to claim 4, wherein the rubber mixture contains a quantity of a polyolefin.

6. A disposable syringe according to claim 5, wherein polypropylene is used as the polyolefin; and the quantity in which it is provided is 1 to 30 wt %.

7. A disposable syringe according to claim 4, wherein the rubber mixture contains a quantity of 0.1 to 2 wt % of a silicone rubber.

8. A disposable syringe according to claim 1, wherein the sealing lip has at least one sealing edge that is delimited on the outside by two conical surfaces that intersect one another.

9. A disposable syringe according to claim 1, wherein the recess comprises a peripheral groove penetrating into the end surface of the piston.

10. A disposable syringe according to claim 9, wherein the hollow cylinder has an end wall, and wherein radially inside the groove the piston has an end surface that has a shape conforming to said end wall of the hollow cylinder.

11. A disposable syringe according to claim 1, wherein the end surface of the piston delimits a projection that extends beyond the sealing lip in the direction of the end wall.

12. A disposable syringe according to claim 11, wherein the piston comprises an excess length at its proximal side and this excess length is dimensioned so that the radial displacement of the sealing lip that results when the piston is pressed against the end wall substantially fills the groove.

13. A disposable syringe according to claim 10, wherein the end surface is interrupted by at least one recess, running radially, that extends from the outer circumference to the center of the piston.

14. A disposable syringe according to claim 8, wherein the recess comprises a peripheral groove penetrating into the end surface of the piston.

* * * * *